United States Patent [19]

Simada et al.

[11] Patent Number: 4,573,466
[45] Date of Patent: Mar. 4, 1986

[54] SURGICAL EQUIPMENT

[75] Inventors: Tamotu Simada, Akishima; Chiaki Shimbo, Mitaka; Hideyuki Horiuchi, Kokubunji; Masamoto Takatsuji, Tokyo, all of Japan

[73] Assignee: Hitachi, Ltd., Tokyo, Japan

[21] Appl. No.: 383,184

[22] Filed: May 28, 1982

[30] Foreign Application Priority Data

May 29, 1981 [JP] Japan .............................. 56-77241[U]
Apr. 7, 1982 [JP] Japan .................................. 57-56609

[51] Int. Cl.⁴ .............................................. A61B 17/36
[52] U.S. Cl. ............................ 128/303.1; 219/121 LA
[58] Field of Search ..................... 128/303.1, 395–398, 128/303.13, 303.14, 303.17, 303.18, 303.19, 800, 801; 338/100; 219/121 LA, 121 LB, 240; 200/265

[56] References Cited

U.S. PATENT DOCUMENTS

| | | | |
|---|---|---|---|
| 3,089,496 | 5/1963 | Degelman | 128/303.14 |
| 3,404,350 | 10/1968 | Muncheryen | 219/121 LA |
| 3,494,363 | 2/1970 | Jackson | 128/303.14 |
| 3,622,743 | 11/1971 | Muncheryen | 128/303.1 |
| 4,163,204 | 7/1979 | Sado et al. | 338/100 |
| 4,273,127 | 6/1981 | Auth et al. | 128/303.1 |
| 4,470,414 | 9/1984 | Imagawa et al. | 128/303.1 X |

*Primary Examiner*—Lee S. Cohen
*Attorney, Agent, or Firm*—Antonelli, Terry & Wands

[57] ABSTRACT

A surgical equipment for transmitting surgical output power such as laser beam from a hand piece is provided with a pressure sensing element of which resistance changes with the force externally applied to the hand piece so that the pressure sensing element senses an operator holding the hand piece.

44 Claims, 24 Drawing Figures

FIG. 4 PRIOR ART
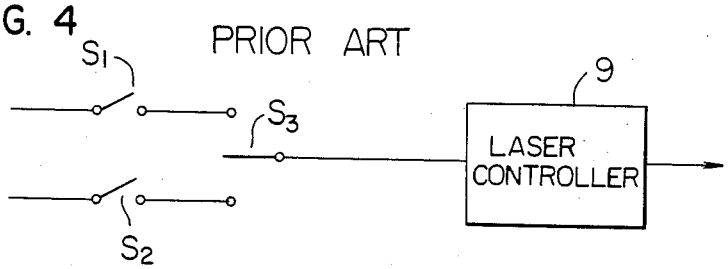
FIG. 5
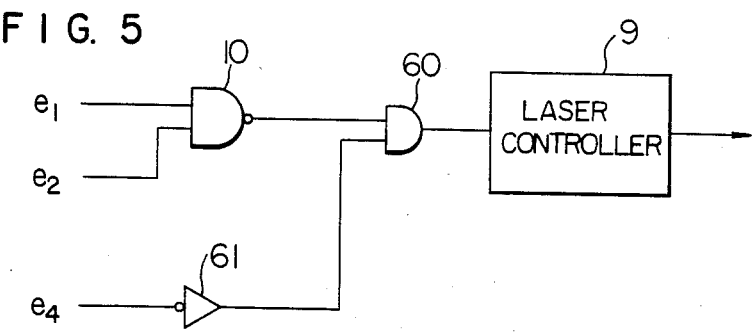
FIG. 6

SURGICAL EQUIPMENT

BACKGROUND OF THE INVENTION

The present invention relates to a surgical equipment and more particularly to a surgical equipment for surgical operation.

In the surgical operations in hospital, in recent years, the conventional surgical steel knife has gradually been replaced by a laser surgical knife using laser beam, an electrosurgical knife using high frequency induction heating, and ultrasonic surgical knife by ultrasonic vibration.

In FIG. 1 illustrating a scheme of a laser surgical equipment, a laser beam is generated by a laser oscillator 1, for example, a carbon dioxide gas laser, and is guided to a proper location by a waveguide 2 such as a multi-joint reflection mirror type manipulator or an optical fiber. The laser beam then is collected and emitted by a hand piece 3 provided at the distal end of the waveguide. During the course of the surgical operation, an operator operates the hand piece 3, actuates a foot switch 5 to oscillate the laser oscillator by a signal through the switch, and emits the laser beam at a predetermined diseased part 4 of a patient 8 laid on an operation table 7. In this way, the operator performs operations such as cutting and coagulation of blood.

Generally, the output of the laser system for the laser surgical knife is approximately several tens W. In using the laser surgical knife, the American safety standard ANSI (American National Standard Institute) Z 136.1, for example, requires the most strict control. In the case of the carbon dioxide laser for the laser surgical knife, a maximum tolerable dosage for the eyes is 0.72 mW. When a patient receives the laser beam from the laser surgical equipment on the skin or eyes, damages suffered would be great.

From the safety standpoint, the (prior) laser surgical knife has the following problems.

One of the problems arises when an operator erroneously pushes a foot switch 5 while not grabbing the hand piece 3. The operator, during his operating work, does not always take or hold the hand piece 3. When he does not take it, it is postured at a given position by a counter balance 6, as shown in FIG. 2. When the hand piece 3 is put on the operation table 7, as shown in FIG. 3, the laser beam could be emitted horizontally. When the hand piece 3 is put as shown in FIGS. 2 or 3, if the foot switch 5 is erroneously pushed, the laser beam may radiate any part other than the diseased part, thereby damaging the patient or the operator.

An arrangement of a prior control circuit for controlling an oscillation of the laser beam in the laser surgical knife is shown in FIG. 4. In the figure, S1 designates a foot switch such as a pedal switch operated when an operator depresses it by the foot; S2 a manually operable switch mounted to the hand piece such as a push switch, a slide volume, a rotary switch; S3 a switch for switching between the switches S1 and S2; 9 a laser controller for controlling a laser oscillator. When the switch S3 selects the switch S2 for the hand piece, there is no danger of an erroneous emission of laser beam. Specifically, when the hand piece is not located on the waveguide or when the operator does not handle the hand piece, the switch S2 is not operated and the laser beam is never radiated. When the switch S3 selects the switch S1, the laser beam is radiated in response to the actuation of the foot switch S1, without regard to the state of the hand piece. During the operation, the operator devotes his attention to his operation work, so that he often fails to check the position of the switch S3. Accordingly, there is a great possibility that he may erroneously depress the foot switch with his foot, while the switch S3 is turned to the S1 position.

As described above, with the known laser surgical knife there is always a high potentiality that the laser beam may be accidently radiated when the laser surgical knife is not operated by the operator. Such an erroneous emission of the laser beam is extremely dangerous to the persons in the operating room.

The importance of preventing the erroneous emission of radiation power for the surgical operations is correspondingly applied for other surgical equipments such as the electrosurgical equipment and the ultrasonic surgical equipment.

The hand piece for the surgical equipment requires in its handling a high skill, since it is directly operated by the operator for effecting the operations.

SUMMARY OF THE INVENTION

Accordingly, an object of the present invention is to provide a surgical equipment with a high safety and a high operability, and free from the erroneous emission of radiation power for surgical operation such as laser beam.

To achieve the above object, in the present invention which is well adaptable for the laser surgical equipment, a sensing means for sensing the operator's holding of a hand piece in the form of a change of voltage is provided in the hand piece. The present invention is improved over the prior art in the following points.

(1) The erroneous emission of the laser beam is prevented to enable an operator to devote himself to his operation work.
(2) The diseased part, the operator, the assistants can be protected from the careless radiation of the laser beam.
(3) The operability of the hand piece equipped with the sensing means is remarkably superior to the prior one with the output switch control means.

BRIEF DESCRIPTION OF THE DRAWINGS

FIG. 4 is a prior laser control circuit used with the laser surgical equipment.

FIG. 5 is a circuit diagram of an embodiment of an oscillation control circuit for the laser surgical equipment according to the present invention.

FIG. 6 shows a schematic diagram of an embodiment of a contacting sensor for sensing the operator's holding of the hand piece used in the present invention.

DESCRIPTION OF THE PREFERRED EMBODIMENTS

Figure 1:
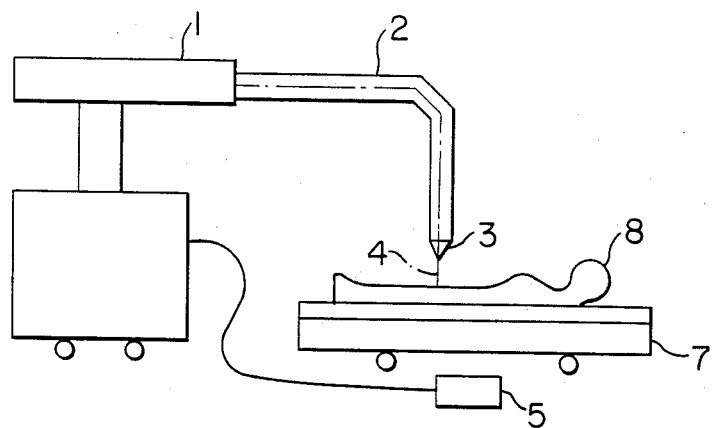
FIG. 1 illustrates a schematic diagram of a laser surgical equipment.
Figure 2:
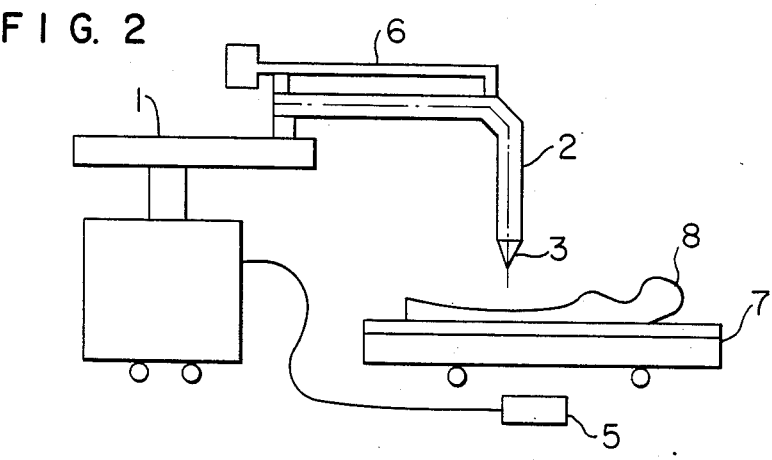
FIGS. 2 and 3 illustrate some states of the hand piece for the laser surgical equipment when it is used.

A circuit arrangement of a major part of a laser surgical equipment or knife, or a control unit for controlling an oscillation of a laser beam, according to the present invention, is shown in FIG. 5. In the figure, e1 designates a signal produced by the foot switch S1 when a laser output is to be projected; e4 a signal produced from a sensing means for sensing the holding of a hand piece by an operator, which is additionally used in the present invention; e2 a signal produced by the switch S2 provided on the hand piece when a laser output is to be projected. In the present embodiment, "ON" and "OFF" of each switch are made to correspond to "low level" and "high level" of each signal and logic levels "0" and "1", respectively. The signals e1 and e2 are coupled with an AND element 60 through a NAND element 10. The signal e4 is coupled with the element 60 through an inverting element 61. With this wiring arrangement, only when the operator holds the hand piece, the output signal from the element 60 is logic "1" to allow the equipment to generate the laser beam. Of course, the "ON" and "OFF" may be made to correspond to "1" and "0", respectively. In this case, the element 10 is an OR gate and the inverting element 61 is unnecessary. With the logic arrangement in FIG. 5, when the operator does not hold the hand piece, even if the foot switch S1 is pushed, the gate element 60 prohibits the signal flow and the operation of the laser control unit 9, thus there is no emission of the laser light.

The signal e2 from the switch S2 mounted on the hand piece is also prohibited when the operator does not hold the hand piece, since the signal e4 from the sensing element for sensing the operator's holding of the hand piece is logic "1". In this case, the laser beam is not produced.

As described above, when the operator does not hold the hand piece, the laser beam is never emitted, ensuring a safety in handling the laser surgical equipment.

The switches S1 and S2 are provided for controlling the oscillation of the laser beam by the operator. Two switches are not necessarily needed, but use of either of the switches is allowable.

FIG. 6 shows a schematic diagram of a hand piece provided with a contacting sensor for sensing the holding of the hand piece by the operator. The switch S2 mounted to the hand piece is omitted in the drawing.

As shown, a plurality of strain sensors 20 are bonded by, for example, adhesive on the periphery of the hand piece 3 at the middle height. As well known, the strain sensor 20 exhibits a change in its internal resistance when pressure is externally applied thereto. If the resistance change is sensed, it can be recognized that the operator holds the hand piece 3. Semiconductor strain gauges, pressure conduction rubber, or the like may be used for the strain sensor. In actual operations, the position of the operator's hand around the hand piece 3 probably changes depending on the operating part of the patient. Allowing for this, the semiconductor strain sensor preferably extends 50 mm in its axial direction of the hand piece.

The resistance change is sensed by a sensing circuit 22 through a signal line 21. The output of the pressure sensor 20 is electrically coupled with the signal line 21 using a pin connector 27. The signal line 21 is further connected to the sensing circuit 22 of which the output signal is coupled with the inverting element 61 shown in FIG. 5.

Figure 7:
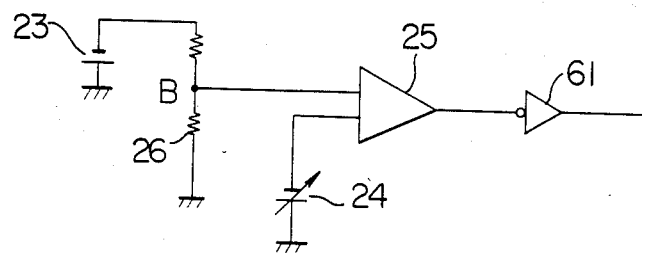
FIG. 7 is a circuit diagram of a sensing circuit of the contacting sensor.

An embodiment of the sensing circuit 22 shown in FIG. 6 is shown in FIG. 7. In the figure, reference numeral 26 designates an internal resistor of the semiconductor strain sensor 20; 25 an operational amplifier of the voltage comparing type; 24 a power source for comparing voltage; 23 a power source of converting a resistance change into a voltage. It is assumed that V is a voltage at a point B when the semiconductor pressure sensor is not in contact with the hand. If the voltage at the point B where the resistance change occurs is $V - \Delta V$, the voltage of the comparing power source 24 is set at $V - \Delta V/2$. More specifically, the output signal from the operational amplifier 25 of the comparing type is $V - (V - \Delta V/2) = +\Delta V/2$ when nothing contacts with the strain sensor contacts.

When the hand piece is not mounted on the waveguide, the resistor 26 shown in FIG. 7 is disconnected from the point B. Then, the output signal from the operational amplifier 25 is $V - (V - \Delta V/2) = +\Delta V/2$ and its logic level is "1". Therefore, the provision of the logic circuit shown in FIG. 5 prohibits the laser oscillator from oscillating in a dangerous state when the hand piece is not being used during the operation. When it is contacted by the hand, $V - \Delta V - (V - \Delta V/2) = -\Delta V/2$ and its logic level is "0". Thus, the laser oscillator is ready for oscillation only when the operator handles the hand piece, thereby ensuring the safety of the patient and the operator.

Figure 8:
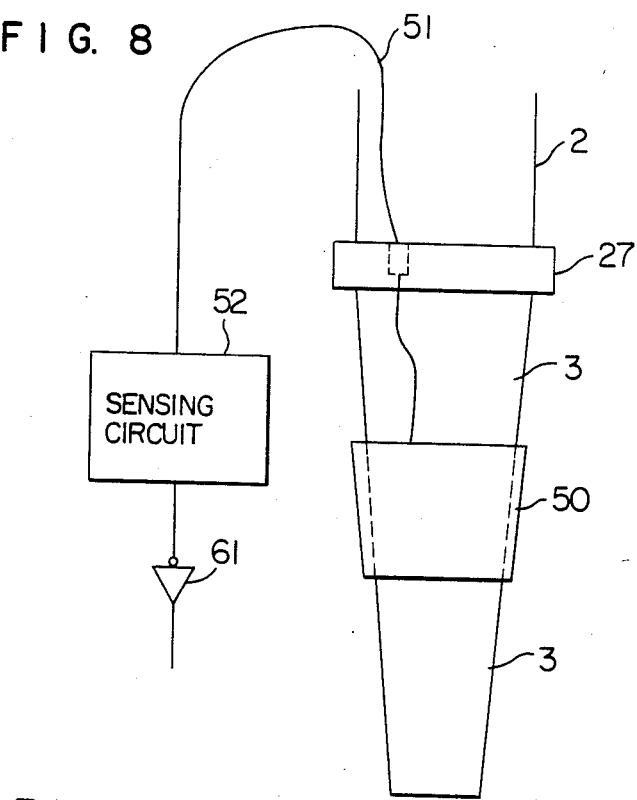
FIG. 8 shows a schematic diagram of another embodiment of a contacting sensor used in the present invention.

Another embodiment of a contacting sensor used in the present invention is illustrated in FIG. 8. In the figure, reference numeral 3 designates a hand piece, and 27 a pin type connector. In the present embodiment, a conductive electrode such as a brass plate, is used for the contacting sensor 50. A signal from the contacting sensor 50 is led through the pin type connector 26 and the signal line 51 to the sensing circuit 52. The output signal is coupled with the inverting element 61 shown in FIG. 5. When the operator grabs the hand piece 3, his fingers contact with the contact sensor 50, so that the holding of the hand piece by the operator is detected.

In this case, the hand piece 3 takes a pencil like shape with 20 mm in diameter and 100 mm in length. The contact sensor 50 is preferably shaped like a sheet of 40 mm in an axial length. For electrically insulating the electrode 50 from the hand piece 3, the electrode 50 is preferably bonded by adhesive such as epoxy resin on the periphery of the hand piece 3 at the middle height.

Figure 9:
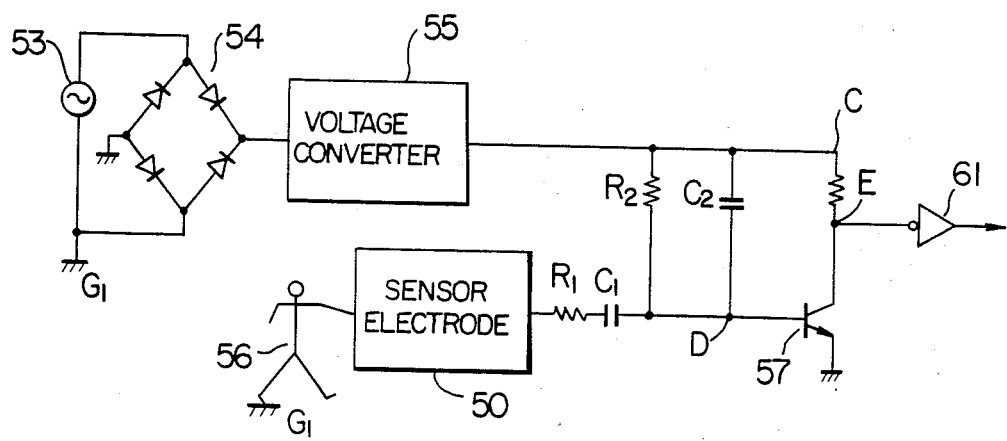
FIG. 9 is a circuit diagram of a sensing circuit of the contacting sensor.

An embodiment of the sensing circuit 52 shown in FIG. 8 is shown in FIG. 9. In the figure, an AC power source 53 is rectified by a bridge-type full-wave rectifier circuit 54. If the AC voltage is 100 V, the rectified DC voltage is converted into a DC 5 V by a voltage converter 55 and is supplied to a transistor 57. When the operator 56 contacts the sensor electrode 50, the voltage across points C and D is given by $$V_{C-D} = \frac{Z2}{Z + Z1 + Z2} V$$

where
Z1: combined impedance of R1 and C1
Z2: combined impedance of R2 and C2
Z: impedance of a human body 56
V: voltage between C and ground G1

When the voltage $V_{C-D}$ is above 0.5 V, the transistor 57 operates and the voltage at the output terminal E changes from 5 V to 0 V. When the hand piece is not located on the waveguide, the contacting sensor 50 is disconnected from its associated circuit. Since the transistor 57 does not operate, the voltage at the output terminal E remains unchanged. When the hand piece is not used, the transistor 57 does not operate, and therefore the laser oscillator does not operate because of the presence of the logic circuit shown in FIG. 5. When the operator contacts the hand piece, the transistor 57 operates to allow the laser oscillator to operate. In this way, the safety in handling the hand piece is secured. The experiment conducted by the inventors showed that a condition providing the most stable operation of the circuit was: R1=43 Mega ohms, C1=2200 pF, R2=1.5 Mega ohms, and C2=150 pF.

As shown in FIGS. 6 and 8, the hand piece 3 widely used is cylindrical and 20 mm in diameter. When the hand piece of such shape and size is placed on the operation table, the semiconductor strain sensor 20 or the electrode type contacting sensor 50 (both referred to as a contacting sensor) contacts the operating table or surgical tools to erroneously operate possibly. To avoid this problem, the contact of the hand piece with the operation table or the surgical tools must be distinguished from the operator's holding of the hand piece. This will be described hereinafter.

Figure 10:
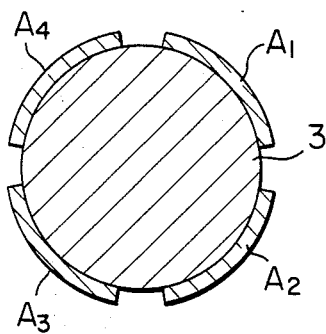
FIG. 10 shows a cross sectional view of another embodiment of a contacting sensor used in the present invention.

FIG. 10 shows a cross sectional view of another embodiment of a hand piece with a contact sensor used in the present invention.

Figure 3:
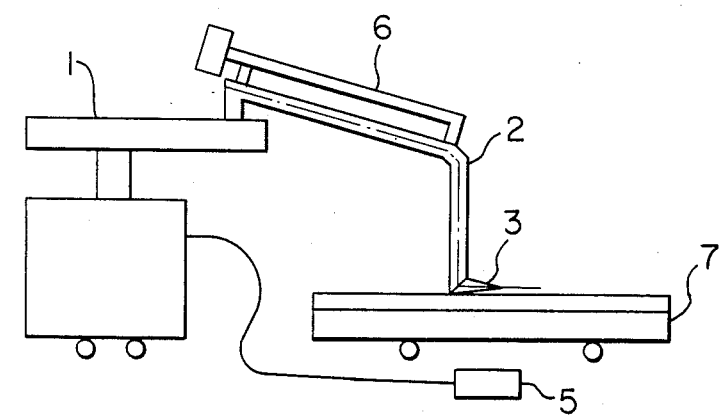
Figure 11:
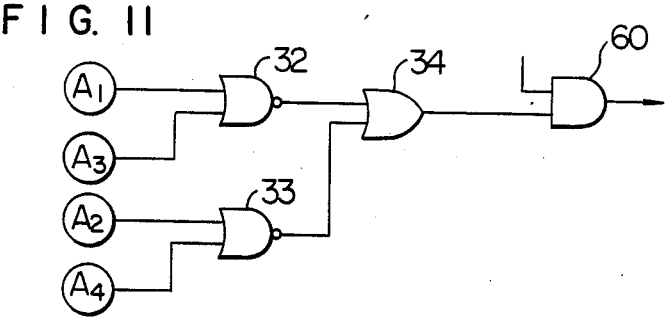
FIG. 11 is a circuit diagram of a leading part of another embodiment of a laser control circuit for a laser surgical equipment according to the present invention.

As shown in FIG. 10, four elements of the contacting sensors A1 to A4 are equidistantly disposed on the periphery of the hand piece 3. For example, in the case of the hand piece of 20 mm in diameter, the peripheral length is about 63 mm. In this case, the width of each sensor may be about 14 mm with an interval of about 2 mm between the adjacent sensors. When the operator grabs the hand piece, at least a pair of the diagonally arranged sensors A1 and A3 or A2 and A4 concurrently contact the operator's fingers so that each sensor of the contacted pair of sensors produces a logical output "0". Then, when the output levels of at least one pair of the sensors are both "0", it is judged by the logic circuit shown in FIG. 11 that the operator operates the hand piece. As shown, the output signals from the sensor pairs A1 and A3, and A2 and A4 are applied to NOR gates 32 and 33, respectively, and then to an OR gate 34. When the sensors A1 and A3 concurrently operate, the OR gate 34 produces a logic "1" output signal, which is applied to an AND gate 60 in FIG. 5 to allow the laser oscillator to be ready for its oscillation. At some angle of the hand when it grabs the hand piece, the contacting sensors A2 and A4 may concurrently operate. In such a situation, the logic circuit shown in FIG. 11 can recognize the same similarly. Thus, when the hand piece is placed on the operation table, as shown in FIG. 3, the contacting sensors diagonally disposed do not operate simultaneously, thereby preventing the erroneous operation.

Figure 12:
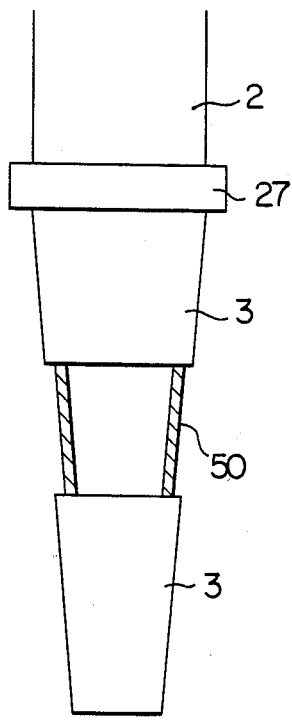
FIG. 12 shows a schematic diagram of another embodiment of a contacting sensor used in the present invention.

A method to discriminate as to whether or not the operator operates the hand piece will be described using an embodiment shown in FIG. 12. FIG. 12 shows a schematic diagram of another embodiment of the hand piece provided with a contacting sensor used in the present invention. In the figure, reference numeral 2 designates a waveguide, 3 a hand piece and 27 a connector for connecting the waveguide and the hand piece. The contact sensor 50 has a diameter smaller than the outer diameter of the hand piece, and is buried axially about 40 mm long and bonded to the hand piece. With such a structure, even when the hand piece 3 is placed on the operating table, the contacting sensor 50 does not directly contact with the operating table, thereby preventing the erroneous operation. When the operator grasps the hand piece 3, his fingers contact with the contacting sensor 50. Thus, it is possible to discriminate as to whether or not the operator grasps the hand piece.

Figure 13:
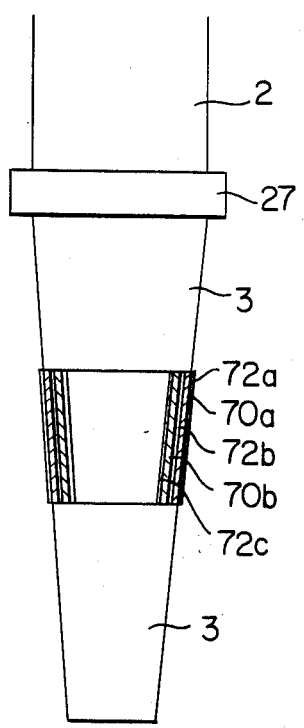
FIG. 13 shows a schematic diagram of an embodiment of a strain sensor according to the present invention.

When the hand piece is provided with the switch S1 for controlling the laser oscillation and the sensing element for sensing the holding of the hand piece, there is a case that the operability is deteriorated when these are located at different positions. In an embodiment to follow, strain sensing elements located at the same position have both the functions of the switch for controlling the laser oscillation and the sensing element for detecting the holding of the hand piece. FIG. 13 shows an example of the hand piece provided with a strain sensing element used in the present invention, in which two strain sensing elements are layered. In the figure, reference numeral 2 denotes a waveguide; 27 a pin type connector; 70a and 70b strain sensing elements; 72a to 72c electrode plates alternately layered which sandwich the strain sensing elements 70a and 70b therebetween. The output signal from the electrode plate 72a as a signal e4 representing the holding of the hand piece and the output signal from the electrode plate 72c as a signal e2 for driving the laser oscillator are led to the logic circuit shown in FIG. 5, by way of a pin type connector 27 and a signal line (not shown). The electrode plate 72b is earthed.

The strain sensing elements 70a and 70b may be pressure-electric conductive rubber or the semiconductor strain gauge, for example, of which resistance decreases upon application of external force.

The strain sensing element 70a uses material or structure of which the sensitivity against the pressure is high. The strain sensing element 70b uses material or structure of which the sensitivity against the pressure is low. With such a construction, when the operator holds the hand piece, the resistance value of the pressure sensing element 70a remarkably decreases by the holding pressure applied and the electrode plates 72a and 72b conduct, thereby to produce a signal e4. Further, when the operator presses the strain sensing element 70b by his fingers, the resistance value rapidly decreases, so that the electrode plates 72b and 72c conduct to produce a signal e2.

Accordingly, the strain sensing element 70a operates as a sensing element for sensing that the operator holds the hand piece. The strain sensing element 70b operates as a switch for controlling ON and OFF of the laser oscillator by the operator. According to the present embodiment, when the oscillation of the laser oscillator is controlled by the switch (corresponding to the strain sensing element 70b) provided in the hand piece, the sensing element (corresponding to the sensing element 70a) for sensing the holding of the hand piece operates without fail. The operability of the hand piece is remarkably improved compared to the hand piece separately provided with the switch and the sensing element. Alternately, the operator holds the hand piece to operate only the strain sensing element 70a, and under this condition, the oscillation of the laser oscillator is controlled by means of the foot switch.

Figure 14:
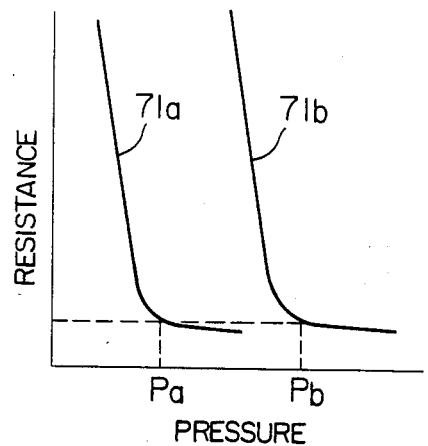
FIG. 14 shows an example of a characteristic of a strain sensing element used in the present invention.

An example of the pressure-electric conductive rubber used for the sensing elements 70a and 70b is shown in FIG. 14. In the figure, curves 71a and 71b indicate characteristics of the sensing elements 70a and 70b, respectively. As shown, the sensing element 70a decreases its resistance with a small pressure applied, and the sensing element 70b decreases its resistance with the pressure larger than the former. With these characteristics, the sensing element 70a is first decreased with the pressure Pa when the finger of the operator contacts with the sensing element mounted in the hand piece, and then the electrodes 72a and 72b on both sides thereof conduct. Further, the operator further forcibly grasps the hand piece to press the sensing elements, the sensing element 70b decreases its resistance with the pressure Pb, so that the electrode plates 72b and 72c on both sides conduct.

The pressure-electric conductive rubber may be the one in which aluminum powder is mixed in the silicon rubber, and a threshold value of the resistance change by the pressure can be adjusted by changing the orientation of the aluminum powder in the rubber. The electrode plates 72a to 72c are conductive metal plates such as aluminum plate or iron plates. The preferable shape of each of the electrode plates 72a to 72c is cylindrical and wound around the hand piece of the pencil type, with a width from 20 to 40 mm. Of course, these may be formed, for example, circularly and disposed only at the portions where the operator's fingers are made to contact.

Figure 15:
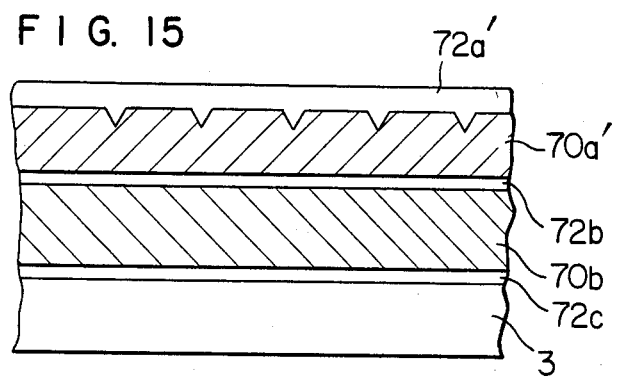
FIG. 15 shows a schematic diagram of another embodiment of a strain sensing element according to the present invention.

In the embodiment shown in FIG. 13, different materials are used for the pressure-electric conductive rubbers of sensing elements 70a and 70b. However similar functions can be attained with the same materials used for the sensing elements, as shown in FIG. 15. FIG. 15 shows a cross sectional view of a major portion of another embodiment of the present invention, in which the pressure-electric conductive rubbers made of the same materials are layered on the outer periphery of the hand piece 3.

The surface of outer electrode plate 72a' contacting with the pressure-electric conductive rubber 70a' is shaped wavy as viewed in cross section. With this shape of the outer electrode plate, even if the pressure-electric conductive rubbers 70a' and 70b are made of the same materials, the pressure-electric conductive rubber 70a' conducts with a smaller pressure than that applied to the pressure-electric conductive rubber 70b. The pressure-electric conductive rubber 70b conducts with a relatively stronger pressure. Thus, the functions similar to those of the embodiment of FIG. 13 can be realized even if the pressure-electric conductive rubbers of the same materials are used.

Figure 16:
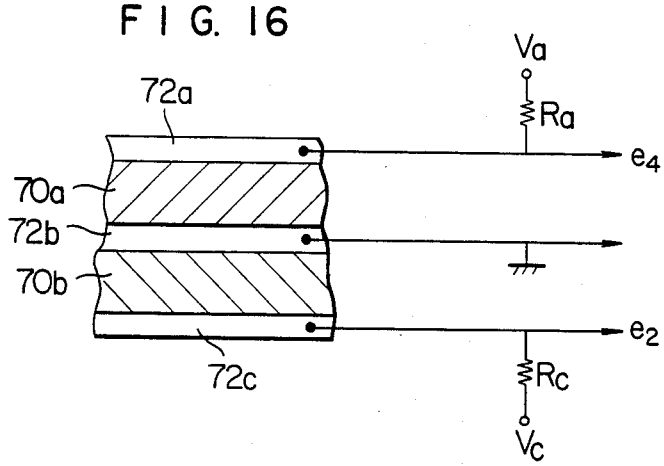
FIG. 16 is a circuit diagram of an embodiment of a signal circuit of the strain sensor according to the present invention.

A method for processing conducting signals produced by the pressure-electric conductive rubbers will be described referring to FIG. 16. DC voltages Va and Vc are applied to the electrode plates 72a and 72c through resistors Ra and Rc, respectively. The electrode plate 72b is grounded. In the present embodiment, resistances of the pressure-electric conductive rubbers 70a and 70b at the pressures Pa and Pb are each approximately 100 ohms, and Ra=Rc=10 K ohms, Va=Vc=5 V. When the resistance of the pressure-electric conductive rubbers are large (when no pressure is applied thereto), the signals e4 and e2 are +5 V, and their logic level is "1". When the resistance is 100 ohms (when pressure is applied), the signals e4 and e2 are approximately 0 V and their logical level is "0". If these signals are applied to the logic circuit shown in FIG. 5, the operation as described referring to FIG. 5 is realized.

As described above, according to the present embodiment, three states of the laser beam, stop, oscillation and preparation, can be set up by laying a couple of sensing elements on the same portion of the hand piece. In the above-mentioned embodiment, the sensing elements are cylindrical in shape, but may be shaped like a strip or a circle.

While in the above-mentioned embodiment the pressure-electric conductive rubber is used for the strain sensing elements, the semiconductor strain gauge may be used with the same effect attained. The semiconductor strain gauge exhibits a characteristic that its resistance changes when pressure is applied thereto, like the pressure-electric conductive rubber and hence can be used for the present invention with the same effects.

Two sensing elements layered in the above-mentioned embodiment may be replaced by a single sensing element.

An embodiment using a single sensing element will be described.

Figure 17:
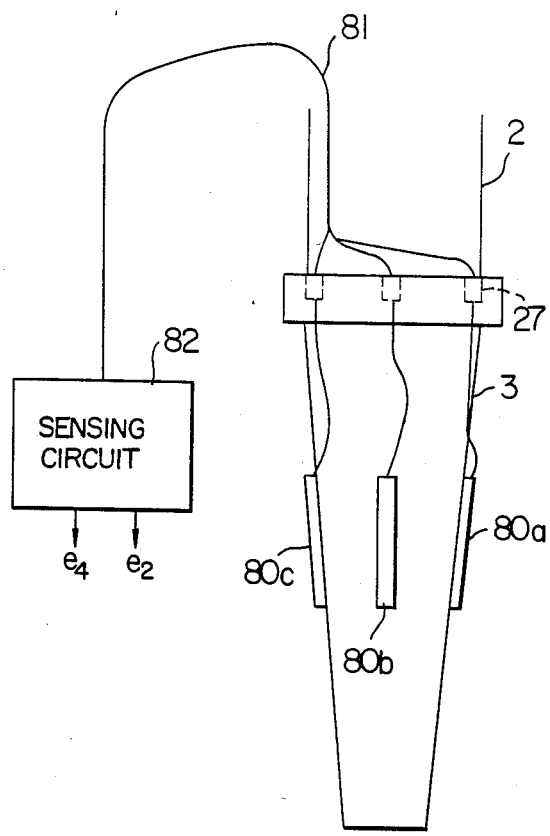
FIG. 17 shows a schematic diagram of yet another embodiment of a strain sensing element according to the present invention.

FIG. 17 shows a leading part of another embodiment of the present invention and illustrates a hand piece provided with a strain sensing element according to the present invention. In the present embodiment, a semiconductor strain gauge is used for the strain sensing element. It is difficult to provide a semiconductor strain gauge with a large area. For this reason, four semiconductor strain gauges 80a to 80d are fixed on the periphery of the hand piece 3 by adhesive, for example, so that the oscillation of the laser beam can be controlled at any location.

The resistance of the semiconductor strain gauge changes substantially linearly against the pressure. Assuming now that the pressure obtained when the operator holds the hand piece is P1 and the pressure when the operator more forcibly grasps the hand piece for oscillating the laser oscillator is P2. The pressures P1 and P2 may be detected in the form of the resistances R1 and R2 by the semiconductor strain gauge.

Figure 19:
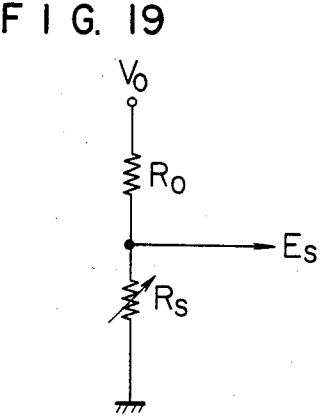
FIG. 19 is a circuit diagram of an embodiment of a resistance-voltage converter circuit for a strain sensor according to the present invention.

How to sense a resistance change due to the pressure of the semiconductor strain gauge will be described. FIG. 19 illustrates the principle of sensing a resistance change. The internal resistance Rs of the strain gauge and a fixed resistor Ro are connected in series and a voltage Vo is applied across the series circuit. At this time, a voltage Es at the connection point between the resistors Ro and Rs is given by $$Es = (Rs/(Ro+Rs)) \times Vo.$$

Figure 18:
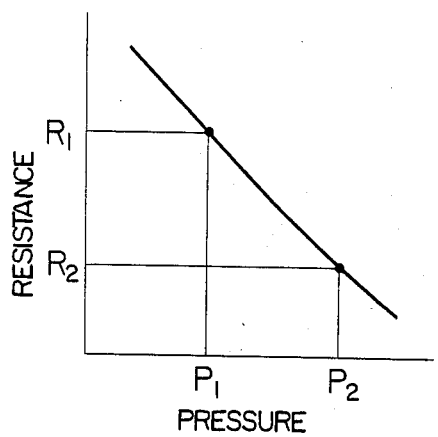
FIG. 18 shows an explanatory diagram of a characteristic of the strain sensor shown in FIG. 17.
Figure 20:
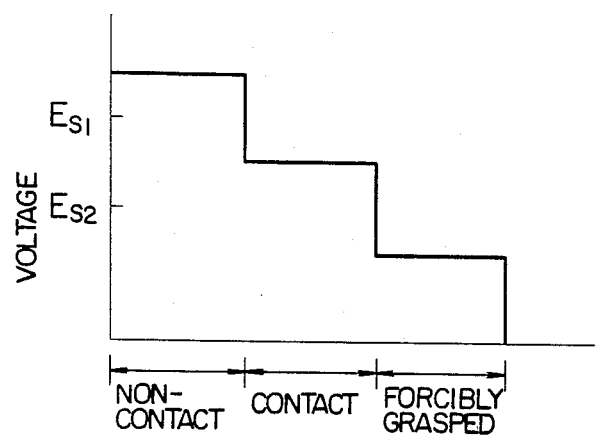
FIG. 20 shows a graph illustrating a relationship between a strain of a strain sensor according to the present invention v.s. voltage.

The resistance Rs of the semiconductor strain gauge monotonously decreases against the pressure, as shown in FIG. 18. Accordingly, the output voltage Es also monotonously decreases against the pressure, as seen from the above equation. A relationship of a pressure applied to the semiconductor strain gauge mounted in the hand piece and the output voltage Es is illustrated in FIG. 20. The output voltage Es changes, as shown in FIG. 20, with respect to a state that he holds the hand piece, and a state that he forcibly holds it. By making use of this relationship, the threshold values Es1 and Es2 are set up. In this case, three types of the pressure states of the semiconductor strain gauge can be sensed. Specifically, the voltages Es1 and Es2 are so selected that the voltage Es when the hand piece is not held is Es>Es1; the voltage Es when it is held is Es1>Es>Es2; the voltage Es when it is forcibly grasped is Es<Es2.

Figure 21:
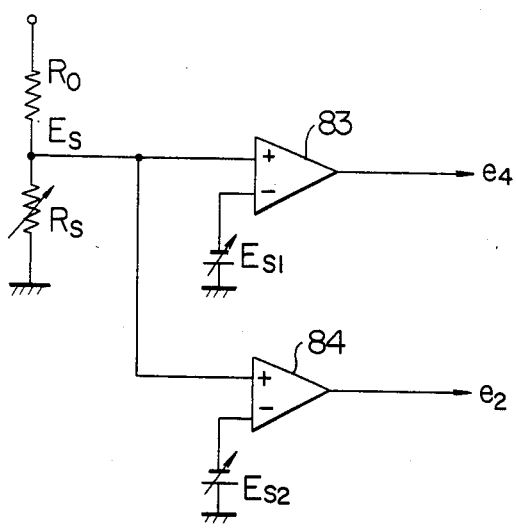
FIG. 21 is a circuit diagram of an embodiment of a strain sensing circuit.

A practical circuit arrangement for sensing the states of the output voltage Es is shown in FIG. 21. The output voltage Es of the semiconductor strain gauge is applied to one of the inputs of each of two voltage comparators 83 and 84. The threshold voltage Es1 is applied to the other input of the comparator 83, and the voltage Es2 is applied to the other input of the voltage comparator 84. Accordingly, when the output voltage Es of the semiconductor strain gauge is smaller than the threshold voltage Es1, the signal e4 becomes low in level and logic "0". When the output voltage Es becomes further smaller than the threshold voltage Es2, the signal e2 becomes low in level and logic "0". The level changes of these signals e4 and e2 are related to the pressure-output voltage relationship shown in FIG. 20 in the following.

1. Es>Es1 (noncontact); e4="1", e2="1"
2. Es1>Es>Es2 (contact); e4="0", e2="1"
3. Es<Es2 (forcibly grasped); e4="0", e2="0".

These logics are directly applied to the logic circuit shown in FIG. 5. e4="0" indicates a state allowing the laser oscillation. In this state, the laser oscillator is oscillated by means of the foot switch. The state that e4="0" and e2="0" indicates a laser oscillation when the hand piece is forcibly grasped. In the state that e4="1" and e2="1" (when the hand piece is not held), the laser beam is not emitted when the foot switch is pushed.

As described above referring to FIG. 17, it is practical to mount four semiconductor strain gauges on the periphery of the hand piece. In this case, resistance changes of the four semiconductor strain gauges are sensed by the sensing circuit 82 through the signal line 81. At this time, the output signals from the semiconductor strain gauges 80a to 80d are coupled through the pin type connector 27 and the signal line 81 with the sensing circuit 82 of which the output signal is supplied to the logic circuit shown in FIG. 5.

Figure 22:
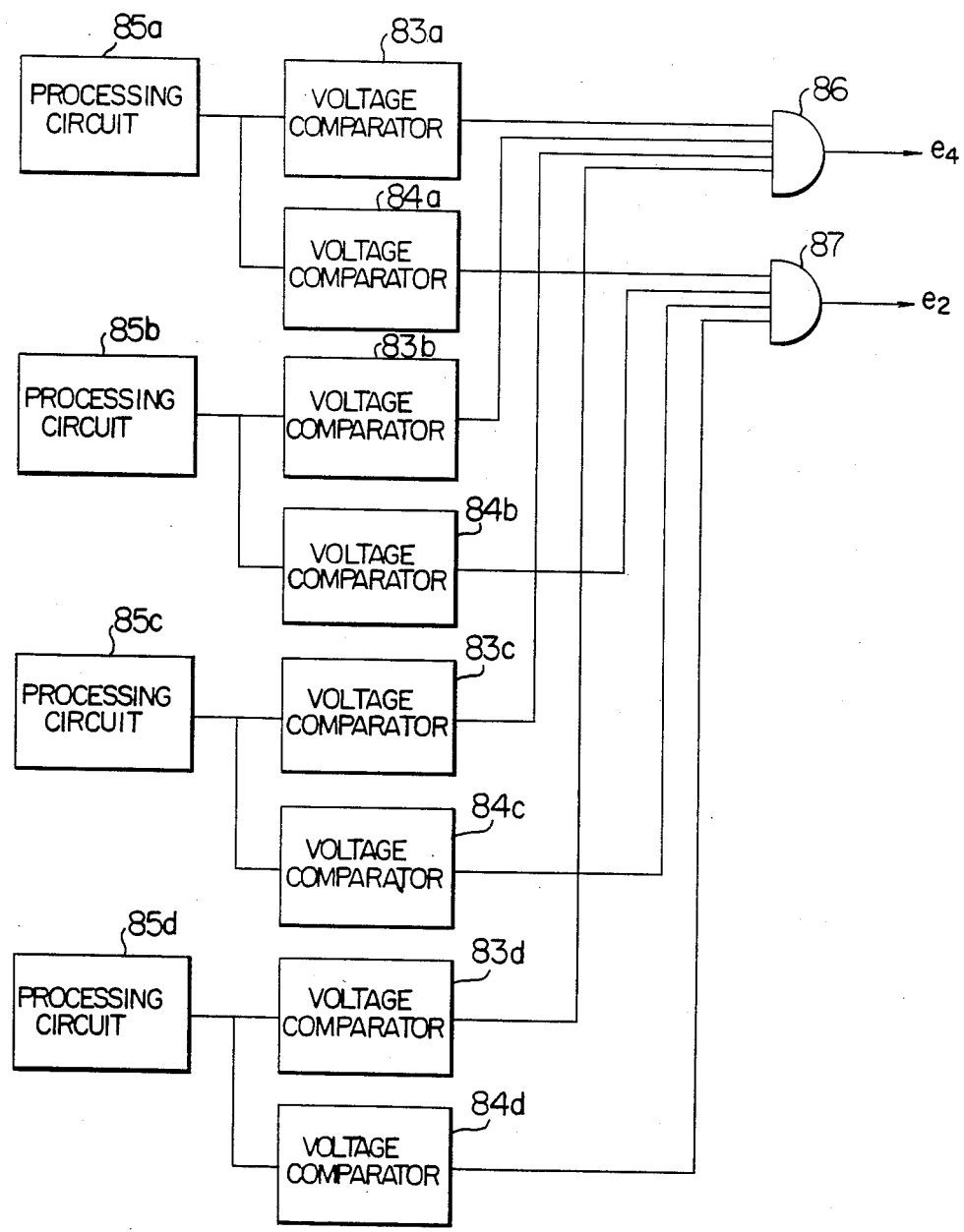
FIG. 22 is a circuit diagram of an embodiment of a signal processing circuit in the embodiment shown in FIG. 17.

A circuit arrangement of an embodiment of the sensing circuit 82 is shown in FIG. 22. In the figure, reference numerals 85a to 85d designate processing circuits for the semiconductor strain gauges 80a to 80d, respectively. The arrangements of these circuits are shown in FIG. 19. Reference numerals 83a to 83d designate voltage comparators for forming the signal e4, and 84a to 84d voltage comparators for forming the signal e2. The output signals from the voltage comparators 83a to 83d are applied to an AND gate element 86 and the output signals from the voltage comparators 84a to 84d are applied to an AND gate element 87. In this way, the signals e4 and e2 are obtained by any one of these signals or a plurality of these signals. With this circuit arrangement, the processing as desired can be performed if any of the four semiconductor strain gauges 80a to 80d operates.

Figure 23:
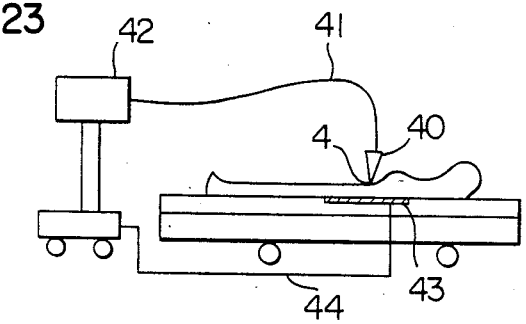
FIG. 23 shows a schematic diagram of an electro-surgical equipment.

While the present invention has been described using the embodiment of the laser surgical knife to which the present invention is applied, it should be understood that the present invention is applicable to the electrosurgical knife currently used in the surgical operations. A scheme of the electrosurgical knife is illustrated in FIG. 23. For performing a surgical operation such as cutting or coagulation of blood, the electrosurgical knife generates a high frequency current of 500 KHz, for example, is generated by a current generating device of a main body 42 and the distal end of the hand piece 40 is made to contact a patient 4. The high frequency current flows through a route; current generating device 42—cord 41—hand piece 40—living body 4—electrode plate pair 43—electrode plate pair cord 44—current generating device 42. A continuous sinusoidal wave is used for the cutting and a pulse wave for the coagulation of blood. A spark discharge or an arc discharge between the end of the hand piece and the living body are used for these surgical operations. As in the case of the laser surgical equipment, the output power is changed between 50 W and 400 W depending on the patient under operation during the course of the operation. In the electrosurgical equipment, the switch between the cutting and the coagulation of blood is made by an operator using a switch provided in the hand piece 40. The output power is adjusted by a nurse according to the direction by the operator. Therefore, the output control system according to the present invention is applicable for the electrosurgical equipment. The switch provided in the hand piece 40 may have the same construction as that of the sensing element shown in FIG. 6, 8, 10, 12, 13, 15 or 17. The current generating device 42 may be ON-OFF controlled by the logic circuit of FIG. 5 or 11.

Figure 24:
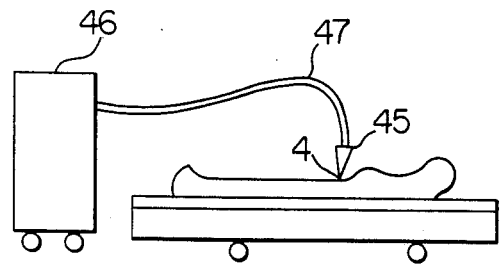
FIG. 24 shows a schematic diagram of an ultrasonic aspirator.

Further, the output control system according to the present invention is applicable for the ultrasonic surgical equipment. The scheme of the ultrasonic surgical equipment is shown in FIG. 24. In the equipment, the hand piece 45 contains a spring like ultrasonic vibrator and a bar like chip. The spring like ultrasonic vibrator (made of nickel, for example) is directly coupled with the bar like chip (made of titanium, for example). A coil is wound around it. The current generated by the high current generating device in the main body 46 flows through a cord contained in the tube 47. At this time, the ultrasonic vibrator repeats expansion and contraction at an ultrasonic frequency while the chip directly coupled therewith does the same operation. The chip repeats these operations with strokes 300 μm maximum to destroy the diseased part 4. The destroyed tissues of the diseased part are absorbed through an absorber tube contained together with the cord in the tube 47.

Accordingly, the output control system according to the present invention is applicable for the control of the output of the current generating device. In more particular, the sensing element shown in FIG. 6, 8, 10, 12, 13 or 15 is provided in the hand piece 45. The output signal from the sensing element is processed by the logic circuit of FIG. 5 or 11. Through this process, the operator can control the start, stop and preparation of the ultrasonic absorber.

As described above, the present invention can control the output of the surgical equipment to operate it with high safety and operability. Thus, the present invention can realize error-free and high reliable surgical equipment.

What is claimed is:

1. A surgical equipment for producing a surgical output power from a hand piece, comprising
    a hand piece connected to a source of surgical output power for applying said surgical output power to an object under operation;
    sensing means provided on said hand piece for sensing an operator holding said hand piece and providing an output in response to said holding;
    control means responsive to the output of said sensing means for enabling said surgical output power to be produced; and
    switch means for controlling the transmission of the surgical output power, said switch means providing an output signal when said switch means is activated, and wherein said control means includes logic means for receiving the output from said sensing means and the output signal from said switch means and allowing the output signal of said switch means to control the transmission of the surgical output power while said sensing means senses the holding of said hand piece.

2. A surgical equipment according to claim 1, wherein said sensing means includes resistor means of which resistance changes with the force externally applied.

3. A surgical equipment according to claim 2, wherein said resistor means is a pressure sensing element.

4. A surgical equipment according to claim 3, wherein said pressure sensing element is made of a semiconductor strain gauge.

5. A surgical equipment according to claim 3, wherein said pressure sensing element is a pressure-electric conductive rubber.

6. A surgical equipment according to claim 5, wherein said sensing means further includes means for applying a constant voltage through a resistor to said pressure-electric conductive rubber.

7. A surgical equipment according to claim 3, wherein a plurality of said pressure sensing elements are provided around said hand piece.

8. A surgical equipment according to claim 1, wherein said sensing means includes means for producing voltage change in response to holding of said hand piece by external force.

9. A surgical equipment according to claim 1, wherein said switch means is foot pedal switch.

10. A surgical equipment according to claim 1, wherein said switch means is a switch means means provided in said hand piece.

11. A surgical equipment according to claim 1, wherein said switch means includes a foot switch and switch means provided in said hand piece.

12. A surgical equipment according to claim 1, wherein said sensing means includes first and second means provided at the same location of said hand piece and having respective resistances which change in accordance with the force externally applied, and said control means includes means responsive to the output from said first means to make ready for the generation of said surgical output power, and responsive to the output of said second means to start the generation of said surgical output power.

13. A surgical equipment according to claim 12, wherein said first and second means include first and second pressure sensing elements, respectively.

14. A surgical equipment according to claim 13, wherein each of said first and second pressure sensing elements includes a pressure-electric conductive member which is formed in the form of a plate having opposing surfaces and rendered conductive with a force larger than a predetermined value, and first and second conductive members provided on said opposing surfaces of said pressure-electric conductive member.

15. A surgical equipment according to claim 14, wherein the pressure-electric conductive member of said first pressure sensing element conducts with a force smaller than that of said second pressure sensing element.

16. A surgical equipment according to claim 14, wherein at least one of said first and second conductive members of said first pressure sensing element has a projection at its surface which contacts with said pressure-electric conductive member.

17. A surgical equipment according to claim 14 or 15 or 16, wherein said pressure-electric conductive member is made of rubber material containing metal powder.

18. A surgical equipment according to claim 17, wherein said rubber material is silicon rubber and said metal powder is aluminum.

19. A surgical equipment according to claim 1, wherein said sensing means includes first means having a resistance which changes according to the force externally applied, and said control means includes first and second comparing means for comparing the output from said first means, respectively, with first and second given set values, and means responsive to the output from said first comparing means to make ready for the generation of the surgical output power and responsive to the output from said second comparing means to start the generation of the surgical output power.

20. A surgical equipment according to claim 19, wherein said first means includes at least one pressure sensing element of which the resistance substantially linealy decreases with increase of the force externally applied.

21. A surgical equipment according to claim 20, wherein a plurality of such pressure sensing elements are provided around said hand piece, each pressure sensing element being coupled with said first and second comparing means.

22. A surgical equipment according to claim 20 or 21, wherein said pressure sensing element is a semiconductor strain gauge.

23. A laser surgical knife equipment comprising a laser oscillator for providing an oscillating laser beam, a waveguide connected to said laser oscillator for transmitting the laser beam therefrom, a hand piece connected to said waveguide for irradiating an object under operation with the laser beam; sensing means provided on said hand piece for sensing an operator holding said hand piece and providing an output in response to said holding; control means responsive to the output from said sensing means for controlling said laser oscillator to make ready for generation of the laser beam; switch means for controlling irradiation of the laser beam, said switch means providing an output signal when said switch means is actuated, and wherein said control means includes logic means for receiving the output from said sensing means and the output signal from said switch means and allowing the output signal of said switch means to actuate said laser oscillator to provide an oscillating laser beam while said sensing means senses the holding of said hand piece.

24. A surgical knife equipment according to claim 23, wherein said sensing means includes resistor means having a resistance which changes with the force externally applied.

25. A surgical knife equipment according to claim 24, wherein said resistor means includes at least one pressure sensing element.

26. A surgical knife equipment according to claim 25, wherein said pressure sensing element is made of a semiconductor strain gauge.

27. A surgical knife equipment according to claim 25, wherein said pressure sensing element is a pressure-electric conductive rubber.

28. A surgical equipment according to claim 27, wherein said sensing means further includes means for applying a constant voltage through a resistor to said pressure-electric conductive rubber.

29. A surgical equipment according to claim 25, wherein a plurality of such pressure sensing elements are provided around said hand piece.

30. A surgical knife equipment according to claim 23, wherein said sensing means includes means for producing voltage change in response to holding of said hand piece by an external force.

31. A surgical knife equipment according to claim 23, wherein said switch means includes a foot pedal switch.

32. A surgical knife equipment according to claim 23, wherein said switch means includes a switch provided in said hand piece.

33. A surgical knife equipment according to claim 23, wherein said switch means includes a foot switch and a switch provided in said hand piece.

34. A surgical knife equipment according to claim 23, wherein said sensing means includes first and second means provided at the same location of said hand piece and having respective resistances which change in accordance with the force externally applied, and said control means includes means responsive to the output from said first means to make ready for irradiation of the laser beam, and responsive to the output of said second means to start the irradiation of the laser beam.

35. A surgical knife equipment according to claim 34, wherein said first and second means include first and second pressure sensing elements, respectively.

36. A surgical knife equipment according to claim 35, wherein each of said first and second pressure sensing elements includes a pressure-electric conductive member which is formed in the form of a plate having opposing surfaces and rendered conductive with a force larger than a predetermined value, and first and second conductive members provided on said opposing surfaces of said pressure-electric conductive member.

37. A surgical knife equipment according to claim 36, wherein the pressure-electric conductive member of said first pressure sensing element is rendered conductive by a force smaller than the pressure-electric conductive member of said second pressure sensing element.

38. A surgical knife equipment according to claim 36, wherein at least one of said first and second conductive members of said first pressure sensing element has a projection at its surface which contacts with said pressure-electric conductive member.

39. A surgical knife equipment according to claim 36 or 37 or 38, wherein said pressure-electric conductive member is made of rubber material containing metal powder.

40. A surgical knife equipment according to claim 39, wherein said rubber material is silicon rubber and said metal powder is aluminum.

41. A surgical knife equipment according to claim 23, wherein said sensing means includes first means having a resistance which changes according to the force externally applied, and said control means includes first and second comparing means for comparing the output from said first means, respectively, with first and second given set values, and means responsive to the output from said first comparing means to make ready for irradiation of the laser beam and responsive to the output from said second comparing means to cause said laser oscillator to irradiate the laser beam.

42. A surgical knife equipment according to claim 41, wherein said first means includes at least one pressure sensing element, of which the resistance substantially linearly decreases with increase of the force externally applied.

43. A surgical knife equipment according to claim 42, wherein said pressure sensing element is a semiconductor strain gauge.

44. A surgical knife equipment according to claim 42 or 43, wherein a plurality of such pressure sensing elements are provided around said hand piece, each element being coupled with said first and second comparing means.

* * * * *